US00PP32236P2

(12) United States Plant Patent
Zaiger et al.

(10) Patent No.: US PP32,236 P2
(45) Date of Patent: Sep. 29, 2020

(54) PEACH TREE NAMED 'ZEE PCH-1'

(50) Latin Name: *Prunus persica*
Varietal Denomination: Zee Pch-1

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 16/602,774

(22) Filed: Dec. 9, 2019

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./194, 197
See application file for complete search history.

*Primary Examiner* — Susan McCormick Ewoldt

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Clingstone fruit with firm, yellow flesh.
4. Fruit having an attractive red skin color.
5. Fruit with good flavor and eating quality.

1 Drawing Sheet

Botanical designation: *Prunus persica.*
Variety denomination: 'Zee Pch-1'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

Prior Varieties

Among the existing varieties of peach trees, which are known to us, and mentioned herein, 'Tra-Zee' Peach (U.S. Plant Pat. No. 6,347), 'Snow Fire' Peach (U.S. Plant Pat. No. 9,470) and the proprietary non-patented peach seedlings '366LH584' and '97GF518'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as an open pollinated seedling selection from the proprietary non-patented peach seedling selection '366LH584'. The seed parent (366LH584) originated from a cross between the proprietary non-patented peach seedling selection '97GF518' and 'Snow Fire' Peach (U.S. Plant Pat. No. 9,470). A large number of these open pollinated seedlings were planted and maintained on their own root system. Under close and careful observation we recognized the desirable tree and fruit characteristics of the present seedling and selected it in 1999 for additional asexual propagation and commercialization.

ASEXUAL REPRODUCTION OF THE VARIETY

In 1999 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and is a regular and productive bearer of large size, yellow flesh, clingstone fruit. The fruit is further characterized by its attractive red skin color and having good storage and shipping ability. In comparison to its proprietary non-patented seed parent (366LH584) the fruit of the new variety has yellow flesh compared to white and is approximately 9 days earlier in maturity. In comparison to the commercial variety 'Tra-Zee' Peach (U.S. Plant Pat. No. 6,347) the fruit of the new variety is clingstone compared to freestone and is approximately 2 days later in maturity with a darker red skin color.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 20 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 20 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies slightly with type and fertility of soil, climatic conditions and cultural practices.

*Form*.—Upright, usually pruned to vase shape.

*Branching habit*.—Upright, crotch angle approximately 45°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 19 consecutive years. No alternate bearing observed.

*Fertility*.—Self-fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 800 hours at or below 45° F.

Trunk:

*Size*.—Medium, average circumference 55.9 cm at 22.9 cm above ground on a 20 year old tree.

*Stocky*.—Medium stocky.

*Texture*.—Medium shaggy, increases with age.

*Color*.—Varies from 10YR 3/4 to 2.5Y 5/2.

Branches:

*Size*.—Medium. Average circumference 19.1 cm at 1.2 meters above ground. Crotch angle approximately 45°, increases with heavy crop load.

*Surface texture*.—New growth relatively smooth. Mature growth medium rough, roughness increases with age.

*Lenticels*.—Average number 27 in a 25.8 square cm area. Average length 4.2 mm. Average width 2.3 mm. Color varies from 10YR 6/8 to 10YR 5/8.

*Color*.—New growth varies from 5GY 5/6 to 5GY 4/6. Mature growth varies from 10YR 3/4 to 2.5YR 3/4, varies with age of growth.

Leaves:

*Size*.—Large. Average length 136.0 mm. Average width 40.1 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 11.3 mm. Average width 1.4 mm. Longitudinally grooved. Surface — glabrous. Color varies from 2.5GY 6/6 to 2.5GY 5/8.

*Glands*.—Type — reniform. Size — large. Average length 1.1 mm. Average diameter 0.6 mm. Number varies from 2 to 4, average number 4. Located primarily on the base of leaf blade and upper portion of petiole. Color varies from 2.5GY 5/6 to 2.5GY 4/6.

*Stipules*.—None present at time of measurement.

*Color*.—Upper surface varies from 5GY 3/4 to 10GY 2/4. Lower surface varies from 7.5GY 3/4 to 10GY 4/4. Midvein color varies from 2.5GY 8/2 to 5GY 7/4.

Flower buds:

*Size*.—Medium to large. Average length 18.0 mm. Average diameter 9.6 mm.

*Hardiness*.—Hardy with respect to California winters.

*Density*.—Dense.

*Form*.—Conical, becoming elongated just before opening.

*Pedicel*.—Average length 3.2 mm. Average width 1.1 mm. Surface — glabrous. Color varies from 5GY 7/6 to 5GY 6/6.

*Color*.—Varies from 5RP 7/10 to 7.5RP 6/12.

Flowers:

*Blooming period*.—Date of First Bloom Mar. 3, 2019. Date of Petal Fall Mar. 13, 2019, varies slightly with climatic conditions.

*Size*.—Large. Average height 22.0 mm. Average diameter 41.8 mm.

*Petals*.—Normally five, alternately arranged to sepals. Size — large. Average height 22.8 mm. Average diameter 18.7 mm. Petal apex — rounded. Petal base — truncate. Form — orbicular. Arrangement — overlapping. Margin — sinuate. Color varies from 5RP 8/6 to 7.5RP 8/4, fades with age of flower.

*Sepals*.—Normally five, alternately arranged to petals. Size — large. Average length 5.6 mm. Average width 5.1 mm. Sepal apex — rounded to triangular. Shape — triangular. Margin- entire. Surface — upper surface glabrous, lower surface pubescent. Color — upper surface varies from 5R 3/6 to 5GY 5/6. Lower surface varies from 5R 2/4 to 5R 2/6.

*Stamens*.—Average number per flower 43. Average filament length 14.7 mm. On average, the stamens are above the height of the petals. Filament color varies from N 9.5/(white) to 7.5RP 6/8. Anther color varies from 7.5R 4/10 to 7.5RP 4/12.

*Pollen*.—Self-fertile. Color varies from 2.5Y 7/10 to 5Y 7/10.

*Pistil*.—Number — normally one. Average length 17.7 mm. Position of stigma even with height of anthers. Surface — pubescent. Color varies from 10Y 8/6 to 2.5GY 8/6.

*Fragrance*.—Slight.

*Color*.—Varies from 5RP 8/4 to 5RP 8/6.

*Pedicel*.—Average length 4.3 mm. Average width 2.6 mm. Color varies from 2.5GY 6/8 to 2.5GY 5/8.

*Number flowers per flower bud*.—Normally one.

Fruit:

*Maturity when described*.—Firm ripe and ready for consumption.

*Date of first picking*.—Aug. 27, 2019.

*Date of last picking*.—Sep. 6, 2019, varies slightly with climatic conditions.

*Size*.—Large. Average diameter axially 72.3 mm. Average transversely in suture plane 78.5 mm. Average weight 258.4 grams, varies slightly with fertility of the soil, amount of thinning and climatic conditions.

*Form*.—Globose.

*Suture*.—Slightly lipped.

*Ventral surface*.—Slightly lipped.

*Apex*.—Slight tip.

*Base*.—Flat.

*Stem cavity*.—Rounded to slightly elongated in suture plane. Average depth 8.4 mm. Average diameter 9.8 mm.

Stem:

*Size*.—Small. Average length 8.1 mm. Average diameter 3.6 mm.

*Color*.—Varies from 2.5GY 5/6 to 2.5GY 5/8.

Flesh:

*Ripens*.—Evenly.

*Texture*.—Firm, meaty.

*Fibers*.—Few, small, tender.

*Firmness*.—Firm, comparable to other commercial peach varieties.

*Aroma*.—Moderate.

*Amydgalin*.—Undetected.

*Eating quality*.—Good.

*Flavor*.—Good, with a good balance between acid and sugar.

*Juice*.—Heavy amount, enhances flavor.

*Acidity*.—Not available.

*Brix*.—Average Brix 13.0°, varies slightly with amount of fruit per tree and climatic conditions.

*Color*.—Varies from 2.5Y 8.5/6 to 2.5Y 8/6 with 5R 3/10 anthrocyanin color around pit area.

*Pit cavity*.—Average length 42.6 mm. Average width 28.9 mm. Average depth 12.0 mm. Color varies from 5R 3/10 to 7.5R 2/6.

Skin:

*Thickness*.—Medium.

*Surface*.—Smooth.

*Pubescence*.—Moderate amount.

*Tendency to crack*.—None.

*Color*.—Ground color varies from 2.5Y 8.5/6 to 2.5Y 8/6. Overspread with 2.5R 3/4 to 5R 4/6.

*Tenacity*.—Tenacious to the flesh.

*Astringency*.—Slight to none.

Stone:

*Type*.—Clingstone, strong adherence to flesh.

*Size*.—Large. Average length 40.6 mm. Average width 26.9 mm. Average thickness 21.9 mm.

*Form*.—Ovoid.

*Base*.—Flat.

*Apex*.—Pointed. Average length 3.1 mm.

*Surface*.—Pitted throughout, pits vary from round to elongated.

*Sides*.—Unequal, one side extending further from suture plane.

*Ridges*.—Relatively smooth, narrow ridges extending from base toward apex.

*Tendency to split*.—None.

*Color*.—Varies from 7.5R 2/4 to 7.5R 2/6 when dry.

Kernel:

*Size*.—Large. Average length 20.5 mm. Average width 10.5 mm. Average depth 6.9 mm.

*Form*.—Ovate.

*Viability*.—Viable, complete embryo development.

*Skin color*.—Varies from 7.5YR 4/8 to 7.5YR 3/6.

Use: Dessert.

*Market*.—Local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

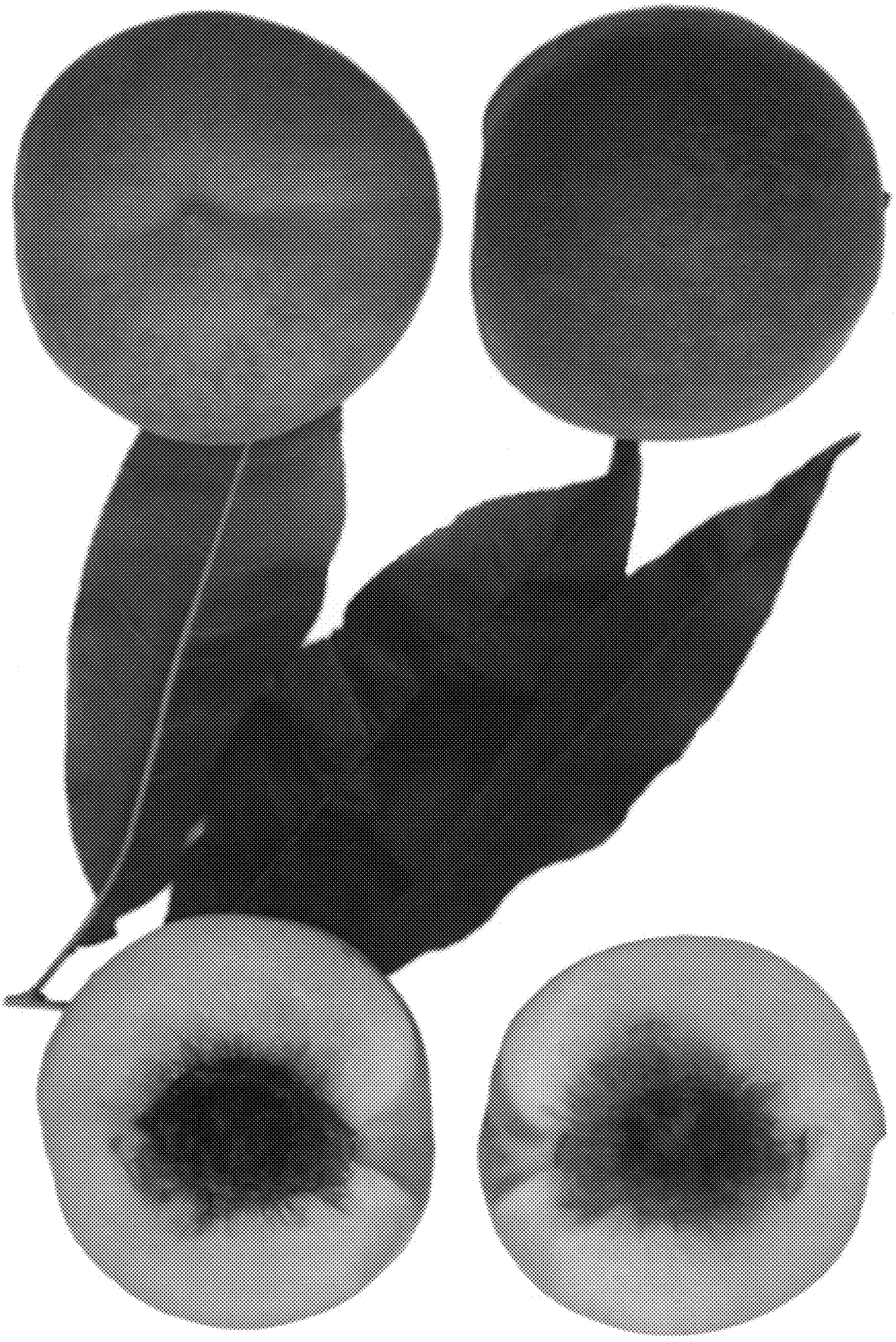

* * * * *